(12) United States Patent
Tatarczyk et al.

(10) Patent No.: US 8,237,828 B2
(45) Date of Patent: Aug. 7, 2012

(54) DEVICE FOR INSPECTION OF PRINT PRODUCTS

(75) Inventors: Christina Tatarczyk, Groebenzell (DE); Joachim Tatarczyk, Groebenzell (DE)

(73) Assignee: Theta System Elektronik GmbH (DE)

( * ) Notice: Subject to any disclaimer, the term of this patent is extended or adjusted under 35 U.S.C. 154(b) by 1229 days.

(21) Appl. No.: 11/409,707

(22) Filed: Apr. 24, 2006

(65) Prior Publication Data
US 2006/0239510 A1 Oct. 26, 2006

(30) Foreign Application Priority Data

Apr. 22, 2005 (DE) .......................... 10 2005 018 855

(51) Int. Cl.
*H04N 9/09* (2006.01)
*H04N 7/18* (2006.01)
*H04N 7/00* (2006.01)
*G06K 9/00* (2006.01)

(52) U.S. Cl. ............ 348/262; 348/86; 348/92; 348/125; 382/112

(58) Field of Classification Search ............... 348/86, 348/88, 92, 93, 125, 128, 262; 382/112, 382/141
See application file for complete search history.

(56) References Cited

U.S. PATENT DOCUMENTS

| | | | |
|---|---|---|---|
| 4,527,874 A * | 7/1985 | Ohmura | 396/73 |
| 4,764,969 A * | 8/1988 | Ohtombe et al. | 382/148 |
| 4,872,052 A * | 10/1989 | Liudzius et al. | 348/126 |
| 5,051,825 A | 9/1991 | Cochran et al. | |
| 5,305,099 A | 4/1994 | Morcos | |
| 5,365,597 A * | 11/1994 | Holeva | 382/318 |
| 5,471,309 A * | 11/1995 | Bolza-Schunemann | 356/394 |
| 5,696,591 A * | 12/1997 | Bilhorn et al. | 356/429 |
| 5,912,988 A * | 6/1999 | Moore | 382/209 |
| 5,999,636 A * | 12/1999 | Juang | 382/112 |
| 6,061,086 A * | 5/2000 | Reimer et al. | 348/125 |
| 6,266,436 B1 * | 7/2001 | Bett et al. | 382/141 |
| 6,404,910 B1 * | 6/2002 | Ungpiyakul et al. | 382/141 |
| 6,738,073 B2 * | 5/2004 | Park et al. | 345/629 |
| 7,212,660 B2 * | 5/2007 | Wetzel et al. | 382/128 |
| 7,376,251 B2 * | 5/2008 | Stober | 382/112 |
| 7,388,968 B2 * | 6/2008 | Rodman | 382/106 |
| 7,627,141 B2 * | 12/2009 | Noffke et al. | 382/112 |
| 7,663,662 B2 * | 2/2010 | Miller et al. | 348/164 |
| 7,664,294 B2 * | 2/2010 | Sacher et al. | 382/112 |
| 2001/0048760 A1 * | 12/2001 | Bett et al. | 382/141 |
| 2002/0026879 A1 * | 3/2002 | Goldstein | 101/486 |
| 2002/0102101 A1 | 8/2002 | Pelletier | |
| 2004/0008773 A1 | 1/2004 | Itokawa | |
| 2005/0043389 A1 | 2/2005 | Roth et al. | |
| 2006/0230358 A1 * | 10/2006 | Sacher et al. | 715/781 |
| 2009/0028417 A1 * | 1/2009 | Floeder et al. | 382/141 |
| 2009/0185028 A1 * | 7/2009 | Ogawa | 348/36 |

FOREIGN PATENT DOCUMENTS

CA 2088816 8/1993
(Continued)

Primary Examiner — John Villecco
(74) Attorney, Agent, or Firm — Gerald E. Hespos; Michael J. Porco

(57) ABSTRACT

A device for inspection of print products (36) produced by a printing machine (10) is provided with a first camera (48) being directed to an inspection field to be checked. At least one further camera (50) is provided being directed at least partially (58) to the same inspection field (54) being checked already by the first camera (48).

12 Claims, 3 Drawing Sheets

FOREIGN PATENT DOCUMENTS

| | | |
|---|---|---|
| EP | 0410253 | 1/1991 |
| EP | 0 522 301 | 1/1993 |
| EP | 554811 A1 * | 8/1993 |
| EP | 0749833 | 12/1996 |
| EP | 0816554 | 7/1998 |
| WO | 01/89834 | 5/2001 |
| WO | 03/067188 | 8/2003 |
| WO | WO 2005/016806 | 2/2005 |

* cited by examiner

DEVICE FOR INSPECTION OF PRINT PRODUCTS

BACKGROUND OF THE INVENTION

1. Field of the Invention

This invention relates to a device in particular for inspection of print products produced by a printing machine, which is provided with a camera particularly for judging the print quality of the print products produced by the printing machine.

2. Description of the Related Art

Devices of the above mentioned kind are used for example with offset printing machines for detecting, if applicable after taking out a sample sheet, possible quality defects visually and/or by technical measurement, e.g. spots, scraps or scraper stripes as early as possible.

Further, it is known to subject printing machines to a permanent quality control, by continuously extracting picture data with a camera and a picture recording arrangement respectively, and analyzing them manually or largely automatically. By doing so, changes of quality of the produced print products can be detected and respective warning notices can be displayed or corrective action on the printing process may be taken.

The individual measurements and judgments to be provided in such quality controls can be manifold and particularly the demand may arise to judge a large inspection field and, furthermore, a single detail with the one camera in use. In order to render this possible, in known picture inspection systems for printing machines often a zoom camera is used by which the inspection field is viewed with different spatial or local resolutions to be selected manually or automatically.

Though the use of zoom cameras has become widely accepted in picture inspection systems for printing machines since, the technology used therefore is rather susceptible to maintenance and expensive.

It is an object of the invention to provide a device for inspection of print products produced by a printing machine and a respective printing machine, which renders a quality control of the above mentioned kind possible and further allows this quality control to be conducted particularly cost-efficiently.

SUMMARY OF THE INVENTION

This object is achieved according to the invention by a device of aforesaid kind for inspection of print products produced by a printing machine, which is provided with a first camera being directed to an inspection field to be checked, and at which at least one further camera is provided being directed at least in sections or partially to the same inspection field being checked already by the first camera. The object is further solved by a printing machine with which such a device according to the invention for inspection of print products is provided. The device according to the invention can particularly be arranged in such a manner, that at the print product running through the printing machine one inspection field at the print product, for example a particular print picture thereon, is viewed at a first location, and then at a subsequent location in the process by the second camera at exactly this print product and print picture, respectively, and in exactly this inspection field a second observation, view or check is made by the at least one further camera.

At the picture inspection system for a printing machine according to the invention not only one single camera is directed to a particular inspections field, but there are provided at least two cameras enabling a check in the inspection field. By means of the several cameras there is particularly not only provided a system by which redundant picture information of the print product is taken or rather picked up, but the several cameras are particularly adapted to different inspection tasks. By doing so, the several cameras being provided according to the invention enable to pick up a large number of different control information out of one single same inspection field at one single view, recording or shooting moment. This can be done without shifting or moving of cameras, which—this will be explained in detail later—has a very positive effect on control times of the quality control and the reaction times during adjusting a printing process.

Aforesaid check according to the invention of a particular inspection field of a print product running through the printing machine can be used for example in such a manner that the first camera is located in front of a dryer and the at least one further camera is located behind the dryer. The picture shooting by the further camera is then targeted to a single print picture already viewed by the first camera in front of the dryer. Thereafter, from this review of the same print picture and in particular by comparing the pictures taken by both cameras quality of the color coating and its drying can be deduced.

According to the invention it is possible to provide very quickly a picture like representation of substantially the entire area of a print product, and, at the same time, to provide a targeted quality control or rather evaluation of single details of the print product. The information can than be used for controlling and ruling of operation processes at the printing machine and of devices, which are upstream and downstream of the machine. The high speed of the check and analysis according to the invention is particularly achieved by not using zoom objectives or rather lenses along with the invention. In particular, known zoom lenses need a rather long time for changing or switching the focal width. This time can be saved by the recording technology according to the invention.

Advantageously, the device according to the invention allows the at least one further camera to be directed only to an inspection field cutout or section of the inspection field checked by the first camera. In other words, by the further camera a detail view within the inspection field of the first camera can be made by the further camera. As always several cameras are available for picture shootings, this detail view can be made simultaneously with an overview shoot. A shifting of e.g. a zoom camera is thereby not necessary. The time saved in that way enables a much quicker reaction of the operators of the printing machine if quality defects arise. Accordingly, defects can also be corrected quicker and thereby the amount of maculation at the printing machine can be reduced significantly by the invention. The lack of a zoom shifting further simplifies the control of the device according to the invention significantly, and thereby reduces the production expenses as well as the operation expenses. The cameras of the device according to the invention further basically can be arranged without moving parts, so the costs for production, maintenance and repair of the device according to the invention can be kept rather low, and in particular the production costs are usually at least not higher than those of a known camera having a respective zoom lens.

Accordingly, by the first camera of the invention it is possible to provide a visual inspection for e.g. recognizing spots, oil splashes, scraps, scratches or coating stripes. The camera provides an evaluation of faults "from a far away viewpoint". By the second camera provided according to the invention, at the same time in particular e.g. a colorimetry, a color density measurement and/or a color register measurement is possible. In doing so, by the second camera in particular a detailed fault evaluation "from a nearby viewpoint" can be provided. The first camera may further serve for simplifying adjustment of the further camera and for simplifying locating the inspection field section on the print product. Further, the second camera may for example be used for a barcode evaluation within the inspection field used by the first camera.

By doing so, advantageously by the further camera a picture having a larger resolution, in particular a larger spatial resolution of an inspection field section of the inspection field observed by the first camera can be provided. Furthermore, by the at least one further camera a higher dynamic of for example up to 4000 grayscales or shades of gray in the picture can be provided.

In order to achieve the advantages mentioned above, further the first camera should advantageously be directed to at least the main part of the actual print picture of the print product.

The at least one further camera should advantageously be directed to at least one measurement mark or markup provided at the actual print picture of the print product, e.g., a cutter mark, a color mark or a register mark. By doing so, a check of register marks at the print product can be provided by the further camera which is according to the invention designed as a camera for details.

In order to be able so provide the above mentioned colorimetry and/or color density measurement in color fields of a printing measurement stripe the at least one further camera should be directed to such a printing measurement stripe located at the actual print picture of the print product, in particular colored. Alternatively or in addition, actual values for the color control of the printing machine can be received from printed areas of the actual print picture by the further camera provided according to the invention.

For the above mentioned visual inspection by means of the device according to the invention, the device should advantageously include at least two displays or pictorial representations, in particular in form of screens, by which the inspection field checked by the first camera and the inspection field checked by the at least one further camera, which is at least partially consistent with the one of the first camera, can be displayed. Alternatively or in addition, even a single screen can be provided, on which several displays or rather representations of the inspection fields can be displayed side by side or at least partially overlapping. The observer or rather inspector may very quickly find a correlation between those two displays, and may thereby be able to judge very well the recognized faults in respect to their relevancy, as well as their basic cause.

In order to allow the observer to find the correlation between the two displays even quicker, advantageously on at least one of the displays a mark should be displayable, by which the inspection field section taken by the at least one further camera is marked within the entire inspection field.

Furthermore, the first and the at least one further camera of the device according to the invention should be arranged in order to be movable together. This moving option can for example be achieved by a transverse, which is located above or in front of the print product to be transported through the printing machine. Additionally or alternatively, the several cameras provided according to the invention should be located together in one casing and/or should be provided with one common illumination. In order to keep the costs for the device according to the invention low in total, the several cameras further should be connected with one common computer for evaluation or rather picture processing. According to the present state of computer technology, therewith the picture data of up to approximately four cameras (which advantageously e.g. observe one overall inspection field and three inspection field sections therein) may be processed.

Alternatively, at the device according to the invention advantageously the first and the at least on further camera are arranged in such a manner that the inspection field of the at least one further camera is movable, in particular shiftable relative to the inspection field of the first camera. The shifting of the inspection fields can thereby be realized by moving the cameras relative to each other (e.g. by a linear motor) or advantageously by a so-called shift-lens, by which the line of vision of a single camera can be changed, if necessary by remote-control. Using shift-lenses can further have advantages in case of inspection fields not movable relative to each other, namely in particular when two cameras shall be directed centrically on a single region at the print product. By the achieved relative movement of inspection field and in particular inspection field section it is also possible, to reach and control several different regions in the superordinate inspection field by the at least one further camera. Furthermore, the further camera can be targeted to regions which, after checking the overall inspection field, are considered to need a checking. Finally, by the shifting of the at least one further camera a realized movement of the product to be examined in front of said cameras can be compensated.

A device arranged in accordance with the invention, in particular completely or partially movable, is located at said printing machine advantageously behind its printing unit, and, when several printing units are provided, in particular behind the last printing unit. Alternatively or additionally the device according to the invention can also be provided e.g. at machines for producing and handling printed sheets, like for example apparatuses for separating, hemming, cutting, collecting, stacking, adding, inserting, sorting and depositing sheets or webs.

Further application examples of the device according to the invention are machines and apparatuses for bookbinding production and subsequent treatment of print products as well as control areas outside of printing machines, which in particular allow a random sampling quality evaluation of the print products. Furthermore, the device according to the invention can also be used in other technical fields, in particular for checking and controlling the surface quality of workpieces, such as sheet metal and/or for detecting material damages. The single cameras used therein may further advantageously be X-ray cameras, ultrasonic cameras, heat sensitive cameras or infrared cameras.

Hereinafter an embodiment of a device according to the invention for inspection of print products produced by a printing machine is explained in further details by means of the attached schematical drawings.

DETAILED DESCRIPTION OF THE PREFERRED EMBODIMENTS

Figure 1:
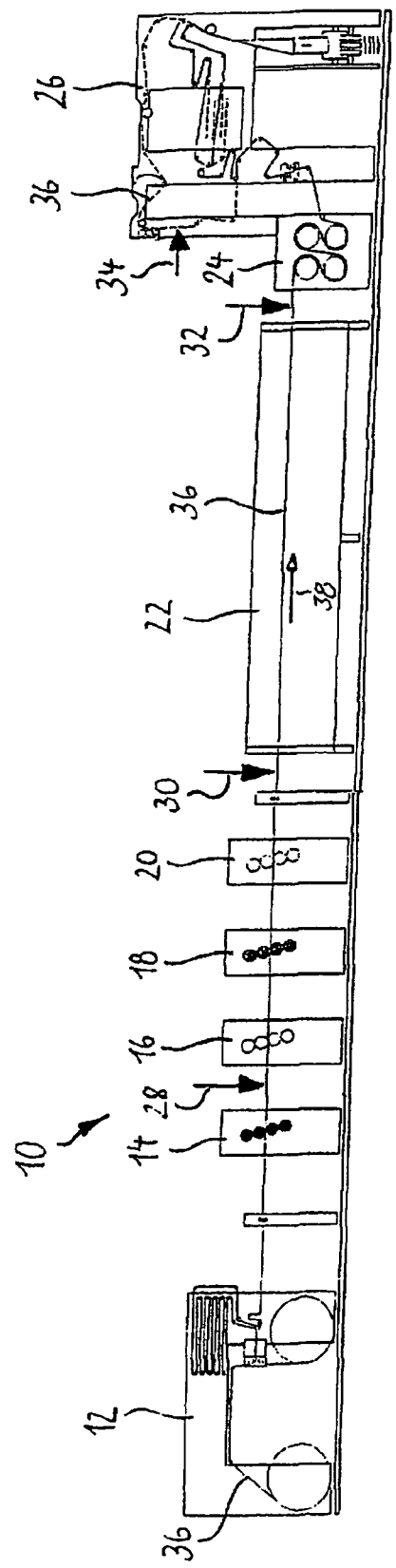
FIG. 1 shows a side view of a printing machine at which at different locations one or several devices according to the invention for inspection of produced print products may be provided.

In FIG. 1 a printing machine 10 is shown which includes as essential elements a roll changer 12 with an integrated retracting unit, in total four print units 14, 16, 18 and 20, a dryer 22, a cooing unit 24 and finally a hemming apparatus including a hemming unit 26. At the printing machine 10 in total four positions for locating one or several inspection devices, which are herein also called device for inspection of print products produced by the printing machine 10 and which will be explained in further details hereinafter, are marked by means of four arrows 28, 30, 32 and 34. The inspection devices are thereby each directed to a paper web 36, which is transported in usual manner through the printing machine 10 along a transport direction 38, and which is thereby provided for example with a color print. In this way, the printing machine 10 serves e.g. as a roll offset machine for the newspaper and/or illustration printing.

Figure 2:
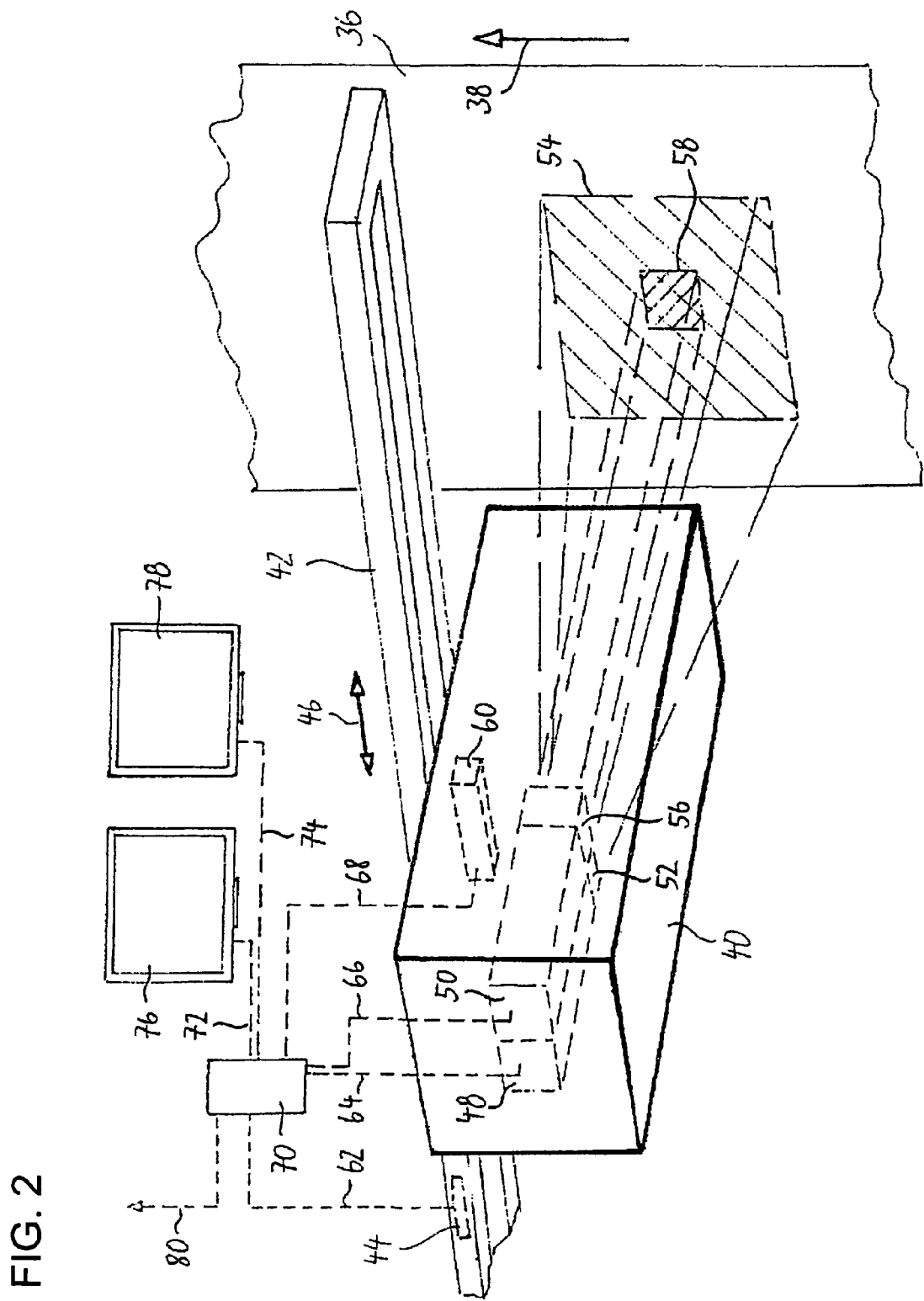
FIG. 2 shows a partial perspective, partially purely schematical view of a first embodiment of a device according to the invention for inspection of print products produced by the printing machine shown in FIG. 1.

In FIG. 2 such an inspection device is shown in detail. FIG. 2 shows said inspection device partially perspectively and partially only very schematical, wherein the perspective part of the drawing corresponds to the arrangement of the inspection device according to arrow 34 shown in FIG. 1. The inspection device is located in this arrangement next to the paper web 36, whose running direction 38 is directed by reference to FIGS. 1 and 2 in the region of the printing machine 10 from bottom to top.

The inspection device thereby includes a substantially cuboid like housing 40, which is attached hanging at a traverse 42. The traverse 42 is arranged substantially in parallel to and in front of the plain of the paper web 36 crossway to the running direction 38. The traverse further includes a slide not shown in further details, at which the housing 40 is fixed and which is slideable along an axis 46 of the traverse by means of a step motor and a tooth belt also not shown in further details, and which can be positioned thereby with an accuracy of approximately 0.05 mm and a speed of up to approximately 0.5 m/sec. Controlling of the movement of housing 40 at the traverse 42 is provided by a traverse control 44 by which in particular the above mentioned, not shown step motor and also not shown reference switches of the traverse 42 are connected.

In the housing 40 a first camera 48 and a second camera 50 are placed, which are located directly side-by-side, and which are both directed to the paper web 36. The first camera 48 is provided with a so called standard lens 52 by means of which an inspection field 54 is observed at the paper web 36. This inspection field 54 includes a substantial part of the real print picture on the paper web 36 and thereby provides a kind of overview picture of the color print provided on the paper web 36. The second camera 50 is provided with a telephoto lens 56 by means of which an inspection field section 58 of the inspection field 54 is observed. This inspection field section 58 is a detail picture with higher spatial or local resolution in the overview picture taken by the first camera 48.

A flashlight 60 is provided in the housing 40 for illumination of the inspection field 54 observed by the first camera 48 and the inspection field section 58 observed by the second camera 50.

The above mentioned elements of the traverse control 44, the first camera 48, the second camera 50 and the flashlight 60 are each connected with a computer 70 depicted purely schematically by lines 62, 64, 66 and 68. At that computer 70 further two lines 72 and 74 are connected which lead to screens 76 and 78. Finally, at the computer 70 a control line 80 is connected which leads to a control of the printing machine 10 not shown.

The computer 70 is adapted to address the traverse control 44 as well as the flashlight 60, further to display the picture information taken by the cameras 48 and 50 on the screens 76 and 78, and, furthermore, to provide a comprehensive picture processing with these information.

In this respect, it is an important aspect that the computer 70 can simultaneously display and evaluate a overview picture as well as a detail picture of print pictures on the paper web 36 because of the dual camera system 48, 50.

As the inspection device particularly works without a zoom camera, a complicated addressing of such a zoom camera and a time consuming shifting of a respective zoom lens can be avoided. Furthermore, the lenses 52 and 56 provided at the cameras 48 and 50, which include fixed focal width, show a lower deformation and a higher resolution in picture quality in particular at the edge of the picture fields in comparison to a zoom lens. Finally, it is not necessary to use a close-up lens or a special lens for taking a close-up view which would considerably reduce the picture quality, thus, sharper and higher-contrast pictures can be provided. As a shifting of a zoom lens is not necessary, the times for recording pictures can considerably be reduced. Furthermore, an overview picture as well as a detail picture can be taken from the print pictures which are moving in front of the cameras 48 and 50 on the paper web 36 running quickly through the printing machine 10. These two pictures, i.e. the overview picture and the detail picture, may then be displayed at the two screens 76 and 78 at the same time. This leads to a better overview at the screens 76 and 78 and a quicker and safer decision making.

Summarizing, by doing so, the print quality at the printing machine 10 can be enhanced very quick, simple and cost effective. As it is, in particular, possible to measure in real time, faults and quality deviations can be found quicker. In this respect it is of particular importance that the pictures simultaneously taken correlate especially good to each other. According to the invention, deviations concerning the illumination, as they may appear at successive shootings, are largely avoided. This altogether leads to a raise of productivity of the printing machine combined with a reduction of costs by reducing the maculation.

In this way, a web observation as well as a quality control combined with a color register measurement and/or an inline color measurement is possible by means of the device according to the invention.

The overview picture provided by the camera 48 also simplifies the setup of position windows of the respective second camera 50 taking the detail pictures. Thus, after such a setting of position windows the housing 40 and the cameras 48 and 50 located therein may be shifted automatically by means of the traverse 42 in a selectable camera position sequence including a definable time process.

Further, by means of the first camera 48 and the second camera 50 a recording can be provided by which a comfortable comparison of pictures via a picture-in-picture representation (PIP) is possible. The picture size of the real taken picture may be chosen substantially free. By means of the camera 48 providing the overview picture and a respective evaluation, furthermore, it is possible to detect when a register mark which should be controlled by the second camera 50 rapidly runs out of the picture field of the second camera 50, e.g. because of a strong deviation of the roller web of the printing machine. It is then possible to track the second camera 50 accordingly by means of the first camera 48.

In the overview picture taken by the first camera 48 it is further possible to selectively superimpose a marker or rather a frame for the detail picture taken by the second camera 50.

While the overview picture in the first camera 48 can further be used for, e.g., an early recognition of coating stripes, by means of the detail picture of the second camera 50 a register mark observation can be made simultaneously. This simultaneous control of several quality features by means of at least two cameras 48 and 50 provides a quicker reaction when quality deviations happen, and thereby does not only lead to a quality improvement but also to a considerable raise in productivity of the printing machine 10 being observed in this way.

Figure 3:
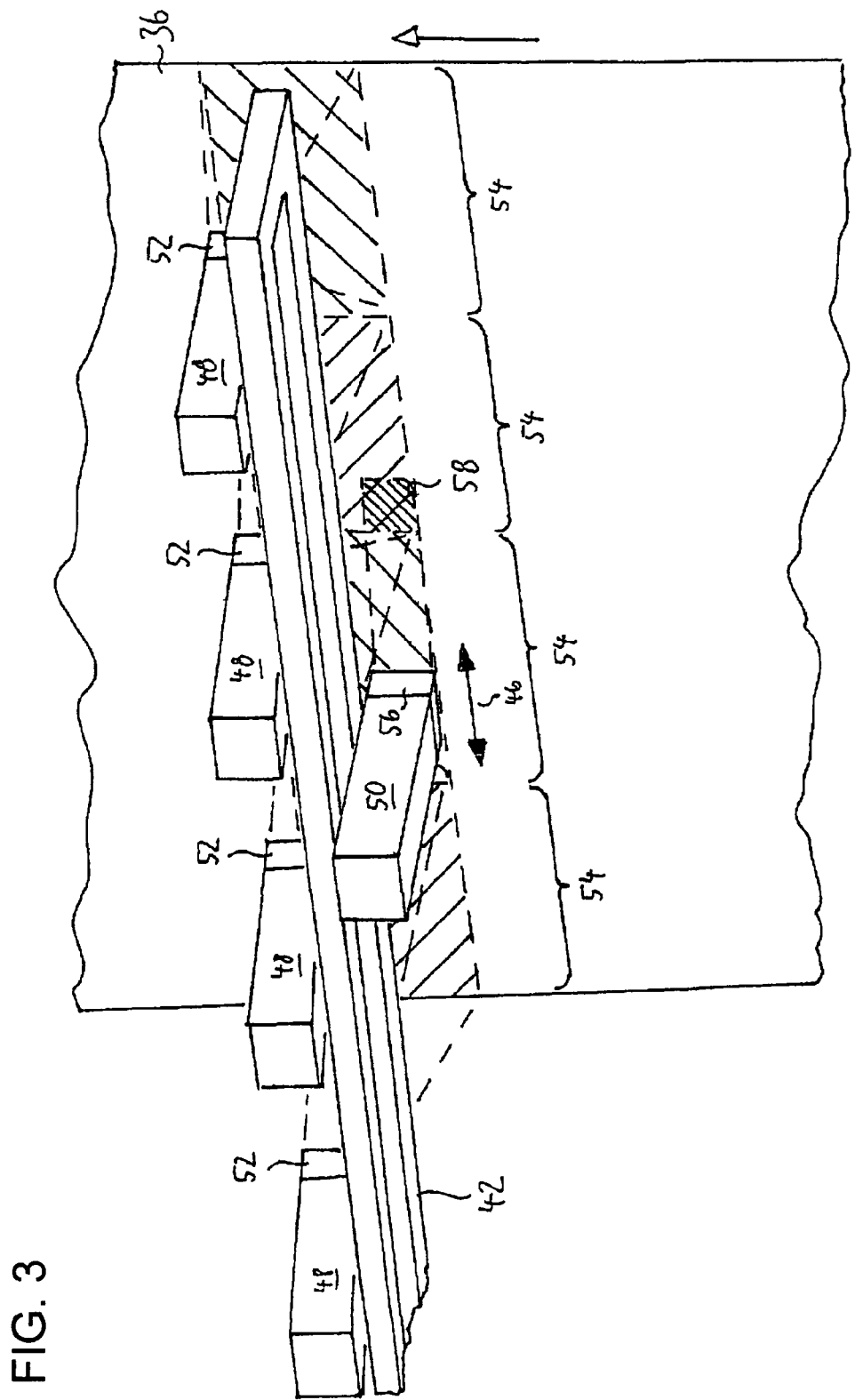
FIG. 3 shows a partial perspective view of a second embodiment of a device according to the invention for inspection of print products produced by the printing machine shown in FIG. 1.

In FIG. 3 an embodiment of an inspection device according to the invention is shown which also includes a traverse 42 in front of a paper web 36 to be observed.

However, in contrast to the embodiment shown in FIG. 2, at the traverse 42 not only one first camera 48 is provided, but there are four such cameras 48 in total located in regular distances at the traverse 42. The four first cameras 48 are each fixed at the upper side of the traverse 42, and are directed, each including a standard lens 52, towards the paper web 36 in such a manner that in total four inspection fields 54 are observed which are located directly side by side (and which are overlapping each other a little). These inspection fields 54 altogether constitute an inspection stripe extending substantially across the entire paper web 36 and at least over the print pictures produced thereon.

At the lower side of the traverse 42 according to FIG. 3 a single so called second camera 50 is attached at a movable slide of this traverse 42, such that it can be moved transversely by means of the traverse 42 (and a non depicted control and evaluation arrangement according to FIG. 2) in front of the paper web 36 in the direction 46.

The camera 50 is further provided with a telephoto lens 56 which is arranged as a shift-lens and which is set up or shifted in that its picture field is always directed to one of the inspections field sections 58 of at least one of the above mentioned inspections fields 54.

What is claimed is:

1. A device for inspection of printed products produced by a printing machine, the device comprising a first camera having a standard lens and capturing an image of an inspection field on the printed product to be checked, and at least one further camera having a telephoto lens, the further camera being pre-focused without zoom shifting on a specific location at least partially within the image of the same inspection field captured by the first camera, wherein the at least one further camera is directed solely to an inspection field section of the inspection field of the first camera and a higher-resolution recording of the inspection field section of the inspection field of the first camera is provided by the at least one further camera, wherein both cameras are directed straight to the printed product for receiving undivided light from the printed product, and wherein the optical axes of the standard lens and the telephoto lens are offset from one another at all locations between the respective lens and the printed product.

2. The device of claim 1, wherein the first camera is directed to at least a substantial part of the actual printed image of the printed product.

3. The device of claim 2, wherein the at least one further camera is directed to at least one measurement mark provided on the actual printed image of the printed product.

4. The device of claim 1, wherein the at least one further camera is directed to a colored printing measurement stripe located at the actual print picture of the print product.

5. The device of claim 1, wherein at least two pictorial representation screens are provided for displaying the inspection field of the first camera and the inspection field of the at least one further camera, the latter inspection field corresponding at least in sections to that of the first camera.

6. The device of claim 5, wherein at least one of the displays displays a mark, by means of which the inspection field section taken by the at least one further camera of the inspection field of the first camera is marked.

7. The device of claim 1, wherein the first camera and the at least one further camera operate at the same time to capture their respective images.

8. The device of claim 7, wherein the further camera is disposed on the device to capture an image of the inspection field section that is at a specified location within the inspection field of the first camera.

9. The device of claim 1, wherein the further camera is configured so that the inspection field section is smaller than the inspection field of the first camera.

10. The device of claim 1 wherein the first camera and the at least one further camera are mounted to a housing in fixed spatial relationship to one another, the housing and the cameras mounted thereto being movable in a transverse direction that is transverse to a transport direction of the printed products.

11. A printing machine including a device for inspection according to claim 1.

12. The printing machine of claim 11, wherein plural print units are provided and the device for inspection is arranged in a feeding direction downstream from the print units, with several of the print units being upstream of the print unit in a downstream-most position.

* * * * *